United States Patent
Koo et al.

[11] Patent Number: 5,840,205
[45] Date of Patent: Nov. 24, 1998

[54] METHOD OF FABRICATING SPECIMEN FOR ANALYZING DEFECTS OF SEMICONDUCTOR DEVICE

[75] Inventors: Jeong-Hoi Koo, Seoul; Doo-Jin Park, Onyang, both of Rep. of Korea

[73] Assignee: Hyundai Electronics Industries Co., Ltd., Kyoungki-do, Rep. of Korea

[21] Appl. No.: 684,451

[22] Filed: Jul. 19, 1996

[30] Foreign Application Priority Data

Jul. 19, 1995 [KR] Rep. of Korea .................. 1995-21184

[51] Int. Cl.⁶ ...................................................... C25F 3/00
[52] U.S. Cl. .............................. 216/109; 216/53; 216/83; 216/95; 438/691; 438/745; 438/749; 438/750
[58] Field of Search ..................................... 438/691, 745, 438/749, 750; 216/53, 83, 95, 109

[56] References Cited

U.S. PATENT DOCUMENTS

| | | | |
|---|---|---|---|
| 3,641,405 | 2/1972 | Brown et al. | 317/235 R |
| 3,647,583 | 3/1972 | De Rouw | 156/6 |
| 4,978,421 | 12/1990 | Bassous et al. | 156/645 |
| 5,131,752 | 7/1992 | Yu et al. | 356/369 |
| 5,191,213 | 3/1993 | Ahmed et al. | 250/310 |
| 5,214,283 | 5/1993 | Le | 250/307 |
| 5,498,871 | 3/1996 | Koo et al. | 250/307 |

OTHER PUBLICATIONS

Grant, J., Hackh's Chemical Dictionary, p. 434, Dec. 31, 1972.

*Primary Examiner*—M. Nuzzolillo
*Assistant Examiner*—Steven H. VerSteeg
*Attorney, Agent, or Firm*—Ware, Fressola, Van Der Sluys & Adolphson LLP

[57] ABSTRACT

A method of fabricating a specimen for analyzing defects of a semiconductor device is disclosed. The method includes the steps of: cutting a wafer to be adjacent to a defective portion that exists in a patterned layer formed on a substrate; molding the first specimen with a resin; grinding the substrate of the first specimen with a predetermined slope; and etching the ground face to expose the defective layer, wherein the wafer includes a semiconductor substrate and patterned layers where memory devices are formed on the semiconductor substrate.

5 Claims, 5 Drawing Sheets

METHOD OF FABRICATING SPECIMEN FOR ANALYZING DEFECTS OF SEMICONDUCTOR DEVICE

CROSS REFERENCE TO RELATED APPLICATIONS

Reference is made to co-owned, copending patent applications (Ser. No. 684,454 filed Jul. 19, 1996, pending) entitled "Method of Fabricating Specimen for Exposing Defects of a Semiconductor Device for Observation and Analysis", and (Ser. No. 684,453, filed Jul. 19, 1996, pending) entitled, "Method of Enabling Analysis of Defects of Semiconductor Device with Three Dimensions", filed on even date herewith and which are hereby incorporated by reference.

FIELD OF THE INVENTION

The present invention relates to a method for analyzing a failure of a semiconductor device, and more particularly to a method of fabricating a specimen for analyzing defects of a semiconductor device that enables to observation of the defects existing in the bottom of the patterned layer of a semiconductor device from the backside.

DESCRIPTION OF THE PRIOR ART

Recently, as a semiconductor device is highly integrated, each layer of a semiconductor device has been changed to an array having a three dimensional, complicated structure to maximize the storage capacitance. As a result, the point of view for the observation of defects existing in a wafer is also required to be in three dimensions.

Among the methods for observing defects of the patterned layer formed on the substrate in a semiconductor device of multi-level structure, top and oblique views have been used to observe the defects from the formed upper layer to the lower layer. Through the above-mentioned methods, however, there are instances where it is impossible to analyze the defects such as with a contact open or misalignment. Therefore, to solve this problem, there has been proposed a method of backside etching that grinds and then etches the backside of a substrate until exposing the patterned layer. In this method, polishing of the backside of the substrate is done mechanically and then processing of the polished surface is done chemically, resulting in the exposure of the defective pattern.

Referring to FIGS. 1A to 1C, the backside etching technology according to an embodiment of the conventional art is described.

First, as shown in FIG. 1A, the upper or outer side of the patterned layer 2 formed on a silicon substrate 1 is molded, resulting in a molded layer 3. All of the substrate 1, the patterned layer 2, and the molded layer shown in FIG. 1A is referred to a first specimen 6. Afterwards, as shown in FIG. 1B, the first specimen 6 is set over a rotatable plate 4 of the polisher with the molded layer 3 facing upward and held in a fixed position. After the setting process, the substrate 1 starts to be polished from the backside by the rotation of the rotatable plate 4 and the polishing process is continued until the substrate 1 is almost removed. Afterwards, residue 5 generated in the polishing process is removed by a mixed solution of $HNO_3$ and HF. Through the above process, a second specimen 7 for the observation of a defective layer is obtained as shown in FIG. 1C.

The conventional method of fabricating a specimen for analyzing the defects of a semiconductor device, however, has a problem that the exposed region of the pattern is irregular and very narrow. Therefore, it is impossible to detect the position of the defective pattern exactly and to designate the end point at which the lower or inner side of the patterned layer starts to be exposed. Resultantly the conventional method has a problem of a high failure rate for fabricating the specimen for the analysis.

In addition, there is also a problem in that it takes much time for the fabrication of the specimen because the silicon substrate 1 has to be wholly polished to expose the formed patterned layer 2. Moreover, as shown in FIG. 1C, the residue 5 of the silicon substrate 1 remains on the surface of the patterned layer because of the irregular polishing rate of the polisher. The result is that the exposed patterns are irregular even if wet etching is completed. In other words, the exposed patterns do not appear in constant positions but as shown in FIG. 1C, appear in here and there. Accordingly, it is impossible to trace the positions of failures.

SUMMARY OF THE INVENTION

Accordingly, one object of the present invention is to provide a method of fabricating a specimen for analyzing defects of a semiconductor device enabling to observation of the position of the defects exactly.

Another object of the present invention is to provide a method of fabricating a specimen for analyzing defects of a semiconductor device enabling to a decrease in the failure rate in fabrication of a specimen due to difficulty in the designation of the end point.

According to the present invention, a method of fabricating a specimen for analyzing defects of a semiconductor device comprises the steps of: making a first specimen of predetermined size by cutting a wafer to be adjacent to defective portion that exists in patterned layer formed on a substrate; molding the first specimen with a resin; grinding the substrate of the first specimen with a predetermined slope; and etching the ground face to expose the defective layer, wherein the wafer includes a semiconductor substrate and patterned layers where memory devices are formed on the semiconductor substrate.

BRIEF DESCRIPTION OF THE DRAWINGS

These and other features, aspects, and advantages of the present invention will become better understood with regard to the following description, appended claims, and accompanying drawings wherein:

DESCRIPTION OF THE PREFERRED EMBODIMENTS

Hereinbelow, referring to the enclosed drawings, preferred embodiments of the present invention are described.

After the fabrication of a semiconductor device such as a DRAM is completed on a silicon substrate 11, any failures like voids or an open metal contact are checked for from a bit map test.

Figure 1A:
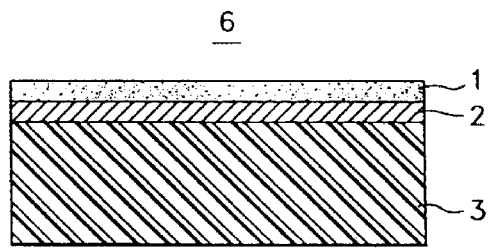
FIGS. 1A to 1C are a method of fabricating specimen for the analysis of defects in a wafer according to the conventional art.
Figure 1B:
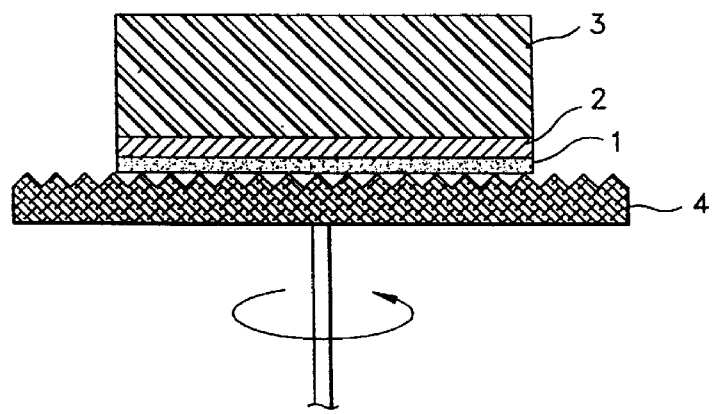
Figure 1C:
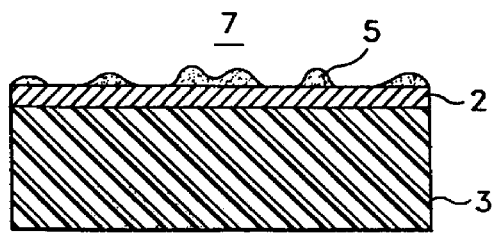
Figure 2A:
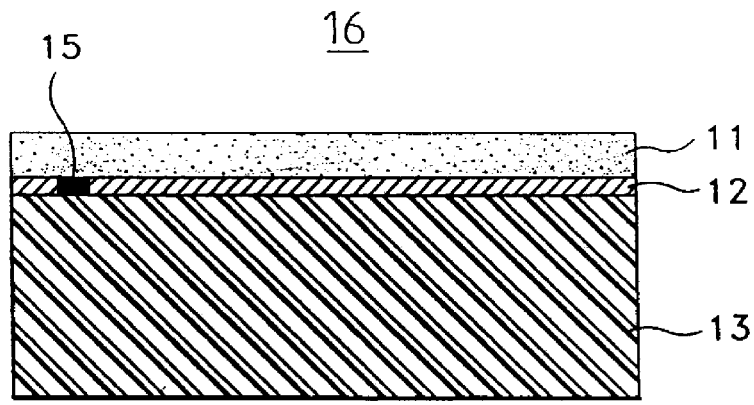
FIGS. 2A and 2B are a method of fabricating a specimen for the analysis of defects in a wafer according to preferred embodiment of the present invention.

Referring to FIG. 2A, in a first step, a first specimen 16 of predetermined size that includes a checked defect 15 is cut by a diamond pencil and is divided from a wafer. An arbitrary portion of the cutting line should be adjacent to the position of the defect 15. Afterwards, with an outer or upper side of the patterned layer 12 facing upward is molded with a resin, resulting in a molded layer 13. This molded layer 13 is to prevent damage to the patterned layer due to the weight of the wafer itself and the pressing weight occasioned upon drilling. Afterwards, the first specimen 16 is turned over with the molded layer 13 facing downward, as shown in FIG. 2A. The solution used for the molding is made by Buehler Company, which has mixed a sample of Kwick powder with a sample of Kwick liquid using a ratio of 1:3 respectively.

Figure 2B:
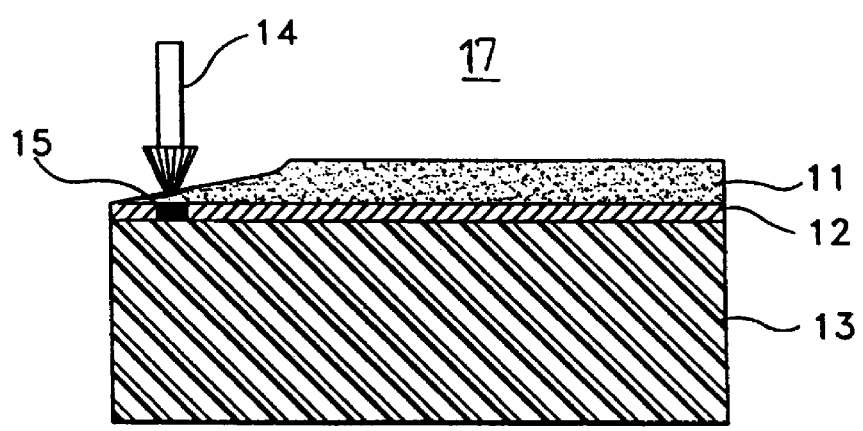

In a second step, as shown in FIG. 2B, a predetermined portion of the backside (an outer side) of the substrate including the defect 15 is ground at a slope of an angle θ to the horizontal face of the substrate by a grinder 14 with a small tip. Afterwards, the ground face is finely polished. The defective position can be more easily exposed as the grinding angle decreases.

In a third step, the polished specimen is etched by using chemicals. Two kinds of etching chemicals are used to expose the patterned layer in the present invention. One is a dilute solution of KOH that roughly etches the polished wafer and the other is a mixed solution of $HF+HNO_3$ that finely etches the roughly etched face. The dilute solution of KOH may, for example, comprise 20 mg of KOH mixed with 300 ml of water thereby having respective mixing ratios of 1:15. The reaction for said dilute solution of KOH occurs only at the polished portion.

After a rough etching step using the solution of KOH is completed, a second fine etching step is done, using a mixed solution of HF and $HNO_3$ e.g., having a mixing ratio of 4:6 respectively. From the result of the previous two etching steps, the patterned layer is exposed. Meanwhile, oxide is exposed at the interface of the patterned layer, which is removed by a rough etching using a solution of dilute KOH. Oxide is one element of patterned layer which includes silicon substrate, oxide, polysilicon, etc. Through the grinding of the backside of the specimen, a predetermined portion of said patterned layer is exposed. Since these exposed faces are ground, they are all etched by the solution of dilute KOH. In particular, since said solution has higher etching selectivity on the oxide than that on the other layers, the oxide layer is more etched.

It is preferred to etch the ground face through the two etching steps using the above solutions. Also, it is possible to use the solution of dilute KOH for rough etching and to use an appropriate solution for fine etching. Moreover, it is possible to use an appropriate solution for rough etching and to use the mixed solution of $HF+HNO_3$ for fine etching.

The above-mentioned present invention can be applied to the observation of defects such as an open metal contact or voids.

Figure 3A:
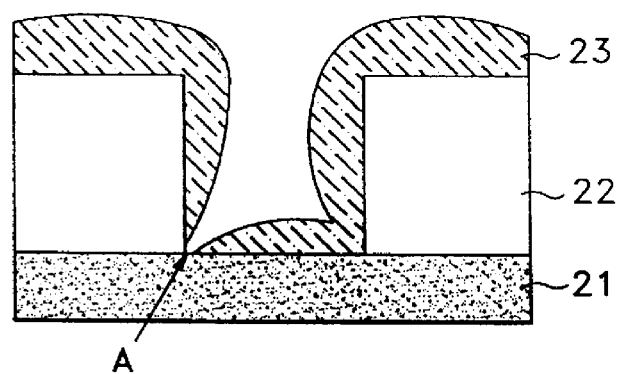
FIGS. 3A and 3B are partial sectional views of a semiconductor device that applies the present invention of FIGS. 2A and 2B to a defect of an open metal contact.

FIG. 3A shows the defect of an open metal contact where an aluminum layer 23 is open at an edge "A" of a contact hole in an insulating layer 22 on a substrate 21.

Figure 3B:
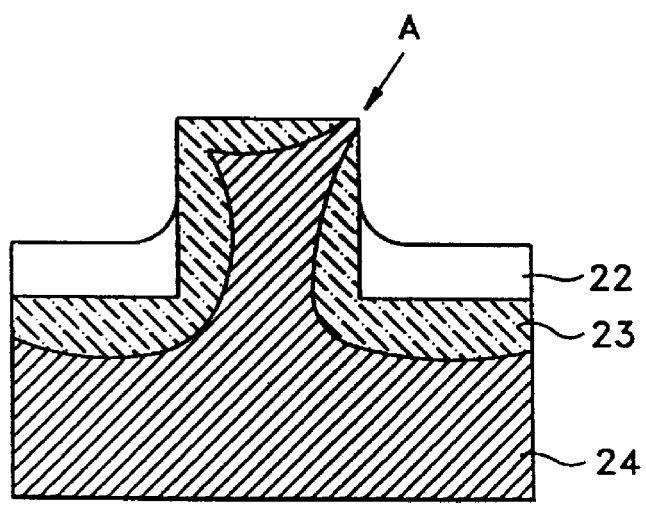

Referring to FIG. 3A, in a first step, a specimen of predetermined size including the checked defect is cut by a diamond pencil and is divided from a wafer. An upper or outer side of the aluminum layer 23 including the contact hole is then molded, resulting in a molded layer 24 as shown in FIG. 3B. Afterwards, as also shown in FIG. 3B, the molded first specimen 25 is turned over with the molded layer 23 facing upward. In a second step, a predetermined portion of the backside of the substrate 21 including the defect is ground at a slope of an angle θ to the horizontal face of the substrate. After the grinding is completed, fine polishing of the ground face is continued.

In a third step, the polished specimen is etched by using chemicals during a rough and fine etching steps as the same method noted hereinbefore.

After the above steps are completed, insulating layer 22 around the contact hole is partially removed by a plasma etching to observe the defect more easily. Afterwards, the defect can be observed by microscopy. It should be realized that the substrate 21 in FIG. 3A could instead be a metal interconnect.

Figure 4:
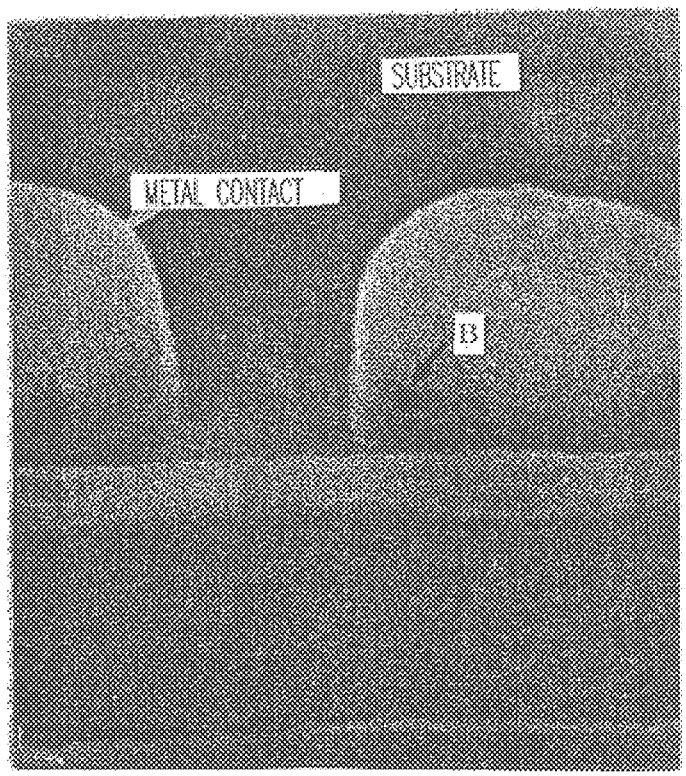
FIG. 4 is a scanning electron microscopy (SEM) photograph showing a contact void failure generated around the periphery of a first metal interconnect, in which a specimen for the photograph is prepared according to the present invention of FIGS. 2A and 2B.
Figure 5:
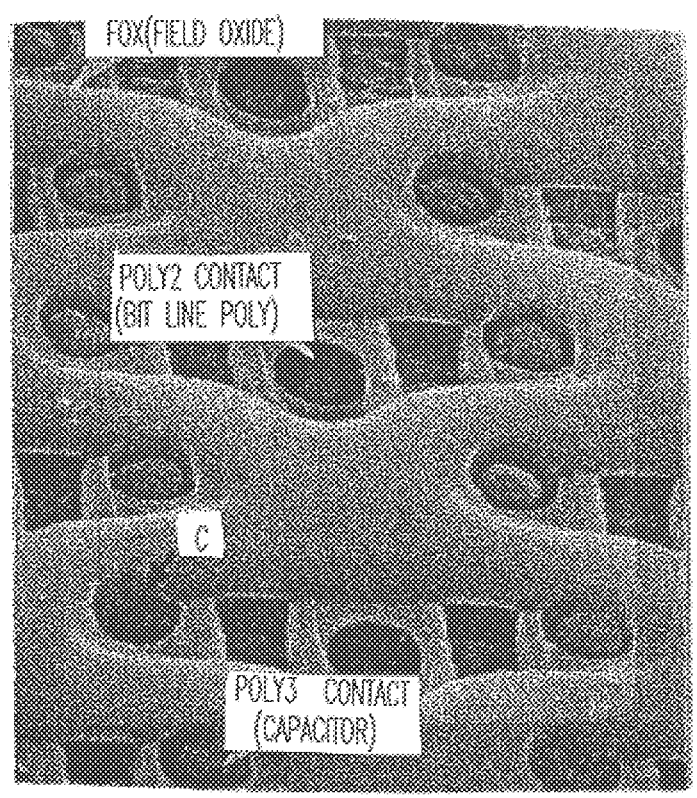
FIG. 5 is a SEM photograph showing a contact open failure generated in a polysilicon contact of a dynamic random access memory (DRAM) cell, in which a specimen for the photograph is prepared according to the present invention of FIGS. 2A and 2B.

FIGS. 4 and 5 are photographs of the ground surface after the grinding, rough and fine etching steps are completed, according to the present invention. While FIGS. 2 and 3 are sectional views, FIGS. 4 and 5 are planar top views of the ground face.

FIG. 4 is a SEM photograph of a metal contact portion in a semiconductor device, in which defects are exposed, according to the present invention. FIG. 4 is a SEM photograph showing a contact void failure generated around the periphery of a first metal interconnect, in which a specimen for the photograph is prepared according to the present invention of FIGS. 2A and 2B. The arrow "B" in the backside photograph shown in FIG. 4 indicates the contact void failure.

FIG. 5 is a photograph showing defects in poly contact portions such as bit line contacts with diffusion regions and capacitors in contact with diffusion regions in a specimen of a DRAM, where defects in poly contacts are exposed, according to the present invention. FIG. 5 is a SEM photograph showing a contact open failure generated in a polysilicon contact of a DRAM cell, in which a specimen for the photograph is prepared according to the present invention of FIGS. 2A and 2B. The arrow "C" in the backside photograph shown in FIG. 5 indicates the contact open failure of a storage node contact polysilicon(or poly 3). In FIG. 5, circular regions are the bottom face of a polysilicon plug for contacting with source or drain.

Besides the above contact defect, a defect due to the misalignment can be also observed using the present method.

As described in hereinbefore, the present invention makes it possible to obtain a homogeneous ground face by defining a grinding portion to a region adjacent to the defective position. From this definition, the grinding processes are more simple and the time spent in fabrication of the specimen decreases. Moreover, the present invention makes it possible to be directly applied to the analysis of failure in a semiconductor device so that it enhances the utility and accuracy of the analysis.

Although the preferred embodiment of the present invention has been disclosed for illustrative purposes, those skilled in the art will appreciate that various modifications, additions and substitutions are possible, without departing from the scope and spirit of the present invention as disclosed in the accompanying claims.

What is claimed is:

1. A method of fabricating a specimen for analyzing defects of a semiconductor device comprising the steps of:

searching for a defective portion that exists in a patterned layer of a wafer, through a bit map test, wherein the wafer includes a semiconductor substrate and patterned layers formed on the semiconductor substrate, wherein the patterned layers comprise memory devices, making a first specimen of selected size by cutting the wafer, the first specimen comprising the defective portion to be adjacent to a cutting line;

molding the first specimen with a resin;

grinding the substrate of the first specimen at a selected slope to form a ground face; and etching the ground face to expose the defective portion.

2. The method according to claim 1, wherein said grinding step comprises a first etching step using a mixture of KOH and water and a second etching step using a mixed solution of HF and $HNO_3$.

3. The method according to claim 2, wherein a solution for said first etching step is a solution of a dilute KOH that has a ratio to water of 1:15, respectively.

4. The method according to claim 2, wherein a solution for said second etching step is a mixed solution of HF and $HNO_3$ with a mixing ratio of 4:6 respectively.

5. The method according to claim 2, wherein a solution for said first etching step is a solution of dilute KOH that has a ratio of 1:15 respective to that of water and a solution for said second etching A is a mixed solution of HF and $HNO_3$ with a mixing ratio of 4:6 respectively.

* * * * *

UNITED STATES PATENT AND TRADEMARK OFFICE
CERTIFICATE OF CORRECTION

PATENT NO. : 5,840,205
DATED : November 24, 1998
INVENTOR(S) : Koo et al.

It is certified that error appears in the above-identified patent and that said Letters Patent is hereby corrected as shown below:

```
Column 1, line 8 after "July 19, 1996" please insert --)--.
Column 1, line 12 after "July 19, 1996" please insert --)--.
Column 1, line 8 after "July 19, 1996)," please delete "pending".
Column 1, line 9 after "entitled" please insert --,--.
Column 1, line 12 before "entitled" please delete "pending".
Column 1, line 22 please delete "to".
Column 2, line 17 after "appear" please delete "in".
Column 2, line 24 after "enabling" please delete "to".
Column 3, line 14 after "facing" please delete "upward" and substitute
--upwards, it--.
Column 4, line 5 after "24" please insert --,--.
Column 4, line 29 after "invention." insert --Thus,--.
Column 4, line 41 after "invention." insert --Thus,--.
Column 5, line 8 (claim 1, line 7) after "devices" please delete
"." and insert --;--.
Column 6, line 13 (claim 5, line 4) after "etching" please delete
"A" and insert --step--.
```

Signed and Sealed this

Thirtieth Day of March, 1999

Q. TODD DICKINSON

Attest:

Attesting Officer

Acting Commissioner of Patents and Trademarks